United States Patent [19]

Pedroso et al.

[11] Patent Number: 6,153,742
[45] Date of Patent: Nov. 28, 2000

[54] GENERAL PROCESS FOR THE PREPARATION OF CYCLIC OLIGONUCLEOTIDES

[75] Inventors: Enrique Pedroso; Ana Grandas, both of Vallirana; Nuria Escaja; Elmostafa Alazzouzi, both of L'Hospitalet del Llobregat, all of Spain

[73] Assignee: University of Barcelona, Barcelona, Spain

[21] Appl. No.: 08/731,202

[22] Filed: Oct. 10, 1996

[30] Foreign Application Priority Data

Oct. 11, 1995 [ES] Spain ................................. 9502023

[51] Int. Cl.[7] ........................... C07H 21/04; C12Q 1/68
[52] U.S. Cl. ............................ 536/25.3; 435/6; 435/91.1; 536/22.1; 536/25.33
[58] Field of Search ........................... 435/6, 375, 91.1; 536/24.3, 23.1, 24.5, 25.3

[56] References Cited

FOREIGN PATENT DOCUMENTS

WO92/17484 10/1992 WIPO .
WO92/19732 11/1992 WIPO .

OTHER PUBLICATIONS

Eritja et al. NPE–Resin, A new approach to the solid–phase synthesis of protected peptides and oligonucleotides I: Synthesis of the supports and their application to oligonucleotide synthesis.Tetrahedron Letters, vol. 32, No. 11, pp. 1511–1514, 1991.

M. V. Rao, et al/Nucleic Acids Research vol. 17, #20 1989 p. 8221–8240.
G. Prakash, et al/Struc. Effects in Rec . . . , 1992 Amer. Chem. vol. 114 p. 3523–3527.
Dolinnaya N. et al/Oligonucleotide circ . . . , 1993 vol. 21, #23, pp. 5403–5407.
Conte M.R. et al/Automated Synthesis of . . . , 12(3&4), 351–358 (1993).
De Napoli L., et al/Facile Prep of Cyclic . . . , 1993, J. Chem. Soc. Perkins Trans. vol. I, pp. 747–749.

Primary Examiner—David Guzo
Assistant Examiner—Janet Epps
Attorney, Agent, or Firm—Michael J. Striker

[57] ABSTRACT

The preparation process starts with a protected nucleotide which is anchored through its phosphate group with an anchoring group that links the phosphate group to a polymeric support, its 5'-hydroxyl group is protected for chain elongation and its 3'-terminal phosphate group is protected with a chain phosphate protecting group. Elongation is carried out under conditions in which the protecting groups of adenine, cytosine and guanine remain unaltered and thymine and uracil groups are not protected. Chain phosphate protecting groups are removed from the obtained cyclic anchored intermediate. Then the product is cleaved from the polymeric support and the protecting groups of the nucleobases are removed. The process has the advantages of general utility for any bases and any size of cycle and of providing high yields with minor by-products. The cyclic oligonucleotides obtained have potential use as antisense products and probes, as well as in therapeutics and in diagnosis.

18 Claims, 6 Drawing Sheets

6,153,742

GENERAL PROCESS FOR THE PREPARATION OF CYCLIC OLIGONUCLEOTIDES

BACKGROUND OF THE INVENTION

1. Field of the Invention

This invention relates to a general process for the preparation of single stranded cyclic oligonucleotides, DNA or RNA, as well as to new intermediates that are necessary to accomplish this process.

2. Description of Prior Art

Cyclic structures of polynucleotides (nucleic acids) are widespread in nature, forming part of the genetic material of many viruses and bacteria. There are single stranded cyclic forms of DNA (viruses) and double stranded cyclic forms of DNA (bacteria and viruses); but only single stranded cyclic structures of RNA are known (viruses).

Although some cyclic oligonucleotides of natural origin are known, most of them are of synthetic origin. The synthesis or preparation of such products has a great interest nowadays for numerous reasons, among which the following can be mentioned: cyclic oligonucleotides are good models to undertake the conformational study of nucleic acids; some of them act as inhibitors of RNA polymerase or as activators of cellulose synthetase; and, most important, single stranded DNA cyclic oligonucleotides with two pyrimidine sequences can hybridize with linear oligonucleotides (DNA or RNA) formed by polypurines, by forming triple helices with high affinity and selectivity, which represents a remarkable ability of molecular recognition that has important uses in the regulation of several biological processes (DNA replication, RNA transcription, RNA processing, translation into proteins, etc.). Promising possibilities of use as antisense oligonucleotides in genetic therapy are derived from the latter reason (for instance, use against different cancers or viral diseases such as AIDS or herpes simplex). Also promising are the possibilities of being used as probes in the diagnosis of numerous diseases, and as markers to locate specific sequences in a chromosome or in other DNA or RNA molecules. Cyclic oligonucleotides can also be used for the site specific targeting of drugs directed to a sequence or fragment of nucleic acid. For all the above-mentioned reasons there is nowadays a great interest in the preparation of cyclic oligonucleotides (see, for instance, patent WO 92/19732).

Until the mid eighties, no specific preparation processes of cyclic oligonucleotides had been described, despite the fact that Khorana et al. isolated the first of such compounds as a by-product in 1958.

At the beginning, all preparation processes involved the phosphate triester method in solution, both for obtaining the linear precursor, and for the cyclization of oligonucleotides with up to 8 nucleobases (see, for instance, M. V. Rao and C. B. Reese, *Nucleic Acids Res.* 1989, vol. 17, pp. 8221–39, and references cited therein). These processes are laborious and time consuming, as a consequence of working in solution. Besides, they have the main drawback of forming all the phosphate diester linkages by using a method that is slow and somewhat ineffective, especially when compared with the phosphite triester method that is routinely used nowadays for the preparation of DNA and RNA fragments.

A preparation process of cyclic oligonucleotides has been described that takes advantage of the triple helix forming ability of some cyclic oligonucleotides, in order to achieve the chemical cyclization of fully deprotected linear oligonucleotides. This process uses a linear template of polypurines that assists the approach of the ends of the oligomer, thus favoring the intramolecular reaction. But this process is limited to the preparation of cyclic sequences that contain two polypyrimidine sequences which allow the formation of the triple helix with the polypurine of the central template. Moreover, another drawback of this process is that it seems to be restricted to the preparation of rather large cyclic molecules. Thus, this process has been used for the preparation of cyclic oligonucleotides from 24 to 46 mer (base residues); but the authors themselves admit that they have failed in obtaining a 16 mer one (cf. G. Prakash and E. T. Kool, *J. Am. Chem. Soc.* 1992, vol. 114, pp. 3523–7; WO 92/17484).

In other cases, chemical cyclization of fully deprotected oligonucleotides has been achieved by using complementary oligonucleotide templates which form a double helix with the end fragments of the structure to be cyclized (cf. N. Dolinnaya et al., *Nucleic Acids Res.* 1993, vol. 21, pp. 5403–7).

In some instances the solid phase synthesis methodology has been used for the preparation of cyclic oligonucleotides, although with poor results. Thus, this methodology has been used by anchoring the oligonucleotide to the polymer through the exocyclic amino group of cytosine, and using insoluble solid supports of polyacrylamide and polyethyleneglycol-polystyrene (PEG-PS) copolymers, as well as a soluble polymeric support of polyethyleneglycol. Even though in the first preparations described the phosphate triester method was used, very recently the phosphite triester method has also been used, with PEG-PS solid supports (cf. M. R. Conte et al., *Nucleosides and Nucleotides* 1993, vol. 12, pp. 351–8 (1993); L. De Napoli et al., *J. Chem. Soc. Perkin Trans.* 1993, pp. 747–9). Nevertheless, one of the main limitations of this process is that the sequence of the cyclic oligonucleotide must contain at least one cytosine (C), since attempts to anchor adenine (A) and guanine (G) to the solid support through their exocyclic amino groups have failed.

In summary, all preparation processes of cyclic oligonucleotides known in the art have limitations or drawbacks that make them of no general use. That is, they are unsuitable to prepare any cyclic oligonucleotide sequence, of any size (until now, medium size cycles have been shown to be the most inaccessible ones).

Furthermore, the processes known in the art make use of chemical methods that are not commonly employed for the elongation of the oligonucleotide chain, for the protection of the bases or for the cyclization reaction, thus preventing the use of the large amount of knowledge related to the preparation of linear oligonucleotides, as well as to the automation of this preparation. Thus, the problem of having a general methodology for the preparation of cyclic oligonucleotides is not satisfactorily solved yet.

SUMMARY OF THE INVENTION

Throughout this specification the following abbreviations, commonly used in the art, will be employed:
DNA: deoxyribonucleic acid
RNA: ribonucleic acid
B: any of the DNA or RNA nucleobases A,C,G,T and U.
A: adenine
dA: 2'-deoxyadenosine
C: cytosine
dC: 2'-deoxycytidine
G: guanine dG: 2'-deoxyguanosine
T: thymine or thymidine
U: uracil or uridine
PS: polystyrene-co-1%-divinylbenzene
PEG: polyethyleneglycol-polystyrene copolymer
(P): a polymeric support (or its radical)
DMT: 4,4'-dimethoxytrityl radical
DCC: N,N'-diclohexylcarbodiimide
Fmoc: 9-fluorenylmethoxycarbonyl radical
Bz: benzoyl radical
iBu: isobutyryl radical
HOBt: 1-hydroxybenzotriazole
CPG: controlled pore glass
CNE: 2-cyanoethyl radical
TCA: trichloroacetic acid
Pyr: pyridine
MSNT: 1-mesitylenesulfonyl-3-nitro-1,2,4-triazole
DCM: dichloromethane
ACN: acetonitrile
DMF: N,N-dimethylformamide
DIEA: diisopropyl ethyl amine
THF: tetrahydrofuran
NMI: N-methylimidazole
TEAA: triethylammonium acetate
TEAB: triethylammonium bicarbonate
Tris: tris(hydroxymethyl)aminomethane
TMG: tetramethylguanidine radical This invention provides a new process for the preparation, through solid phase synthesis, of a single stranded cyclic oligonucleotide of general formula (I), or a salt or solvate thereof,

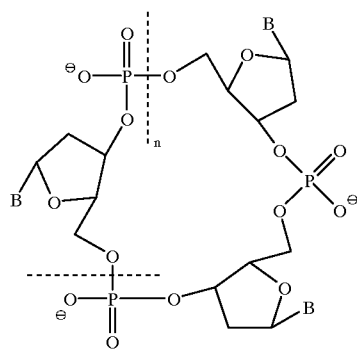

(I)

wherein the B groups are equal or different from each other, and may be any of the common radicals of endocyclic is nitrogen of any of the five nucleobases (T, U, A, C or G); the furanose backbones substituted in the 3' and 5' hydroxyl groups are equal or different from each other, and may be, either biradicals of D-2-deoxyribofuranose (the sugar portion of DNA, drawn in the formula), or biradicals of D-ribofuranose (the sugar portion of RNA, with a 2'-hydroxyl function, not shown in the formula); and n is an integer number between 0 and about 50, preferably between 0 and about 20. This process comprises the following sequence of steps.

Step a):

The starting material is a nucleotide having the general formula (IV), protected and anchored to a polymeric support through its phosphate group, where B' is the radical of any nucleobase, which is not protected in the case of T and U, and which has a standard protecting group on the exocyclic amine group in the case of A, C and G; $R_3$ is a protecting group of the 5'-hydroxyl, which is suitable for the elongation of the chain; $R_2$ is a protecting group of the 3' terminal phosphate; X is the biradical of a protecting/anchoring group, which protects the 3' terminal phosphate and which simultaneously acts as an anchor (or linker) to the polymeric support; (P') is, either the radical of the original polymeric support (P), or the radical of a modified polymeric support that has, in addition, a spacer/bonding group.

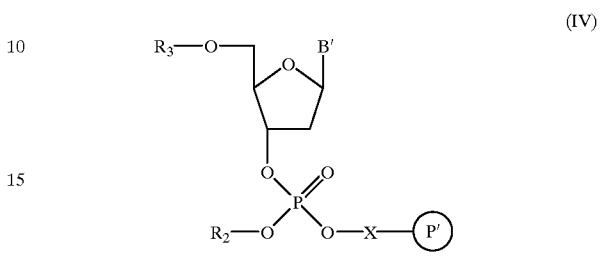

(IV)

Step b):

Either the protecting group of the 3' terminal phosphate is maintained, or it is removed before starting the chain elongation.

Step c):

A sequence of (n+1) conventional steps is carried out for the elongation of the oligonucleotide chain using the nucleotides of the desired bases. The nucleotides are protected in their 5'-hydroxyl groups with protecting groups $R_3$, equal or different from each other, and suitable for chain elongation. The nucleotides are protected in their 3'-phosphates with chain phosphate protecting groups $R_1$, equal or different from each other. These protecting groups are selected in such a way that $R_2$ and $R_3$ are removable under conditions in which $R_1$, X–(P') and the protecting groups of A, C and G in B' remain unaltered. Thus the intermediate oligonucleotide, protected and anchored, having the general formula (III), is obtained:

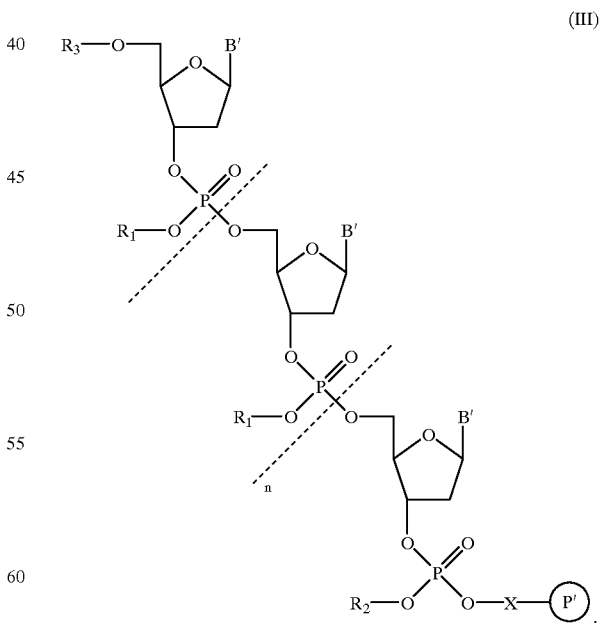

(III)

Step d):

In the intermediate oligonucleotide (III), protecting group $R_2$ (if it has not been previously removed) and protecting group $R_3$ are removed sequentially (in any order); the resulting product is submitted to a cyclization reaction, in the presence of an appropriate cyclizing reagent, and the protected and anchored intermediate cyclic oligonucleotide having the general formula (II) is obtained:

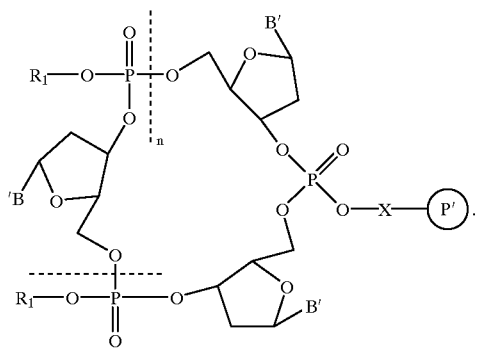

(II)

Step e):

In the intermediate cyclic oligonucleotide (II) the following reactions are carried out simultaneously or sequentially (in any order): removal of the $R_1$ protecting groups of the phosphate chain; cleavage from the polymeric support, and removal of the protecting groups of A, C and G of B'; so that the desired cyclic oligonucleotide of general formula (I) is obtained.

Step f):

Finally, product (I) is submitted to the standard treatments appropriate for isolating the desired salt or the desired solvate (e.g. a hydrate).

In a particular embodiment of the process of this invention, all the chain phosphate protecting groups $R_1$, are equal to each other; the 5'-hydroxyl protecting groups $R_3$ are the same all along the chain elongation; and the nucleobases A, C and G in B' are protected in the same way for each nucleobase.

Preferred subject matter of this invention is the above disclosed process in which the 5'-hydroxyl protecting groups $R_3$, convenient for chain elongation, are selected from the group consisting of 4,4'-dimethoxytrityl (DMT), 4-methoxytrityl (MMT) and 9-(9-phenyl)xantenyl (Pix); the chain phosphate protecting groups $R_1$, are selected from the group consisting of methyl (Me), 2-cyanoethyl (CNE), 2-cyano-1,1-dimethylethyl, allyl and p-nitrophenylethyl; the 3' terminal phosphate protecting group $R_2$ is selected from the group consisting of methyl (Me), 2-cyanoethyl (CNE), 2-cyano-1,1-dimethylethyl, allyl and p-nitrophenylethyl; the biradical X of the protecting/anchoring group is a benzene ring which is linked to the oxygen atom of the 3'-phosphate and to the polymer support (P') through any pair of its six carbon atoms, and which is optionally substituted, in any of the four vacant positions, by a radical $R_4$ selected from the group consisting of Cl, Br, $NO_2$ and $OCH_3$; (P') is, either the radical of an original polymeric support (P), or a modified polymeric radical having the formula —$(CH_2)_m$—CO—Y—NH—(P) with m=0–6, preferably with m=1, where Y is either a simple covalent bond or a biradical having the formula —NH—$(CH_2)_s$—CO— with s=1–10, preferably with s=5; the original polymeric support (P) is selected from the group consisting of polystyrene-co-1%-divinylbenzene (PS), polyethyleneglycol-polystyrene copolymer (PEG-PS), polyacrylamide, polystyrene-Kel F, polyethyleneglycol, silica gel, controlled pore glass, cellulose and teflon, the first three being the preferred ones; and the protecting groups of the nucleobases A, C and G in B' are selected from the set consisting of benzoyl (Bz), isobutyryl (iBu), toluoyl, phenylacetyl, phenoxyacetyl, pivaloyl, dimethylaminomethylene, tert-butylphenoxyacetyl and nitrophenylsulfenyl.

The following combinations of protecting groups are preferred: either $R_2$ is cyanoethyl and $R_1$ is methyl, or $R_2$ is allyl and $R_1$ is cyanoethyl, or both $R_1$, and $R_2$ are cyanoethyl provided that $R_2$ is eliminated before the chain elongation. In a similar way, the following conditions are preferred: $R_3$ is 4,4'-dimethoxytrityl (DMT); biradical X of the protecting/anchoring group is a benzene ring which is linked to the oxygen of the 3'-phosphate through position 1, which is linked to the polymeric support (P') through position 4, and which is substituted by $R_4$=Cl in position 2; the cyclization reagent is 1-mesitylenesulfonyl-3-nitro-1,2,4-triazole (MSNT); the protecting group of the nucleobases A and C in B' is benzoyl (Bz); and the protecting group of the nucleobase G in B' is isobutyryl (iBu).

The chemical elongation of the chain can be carried out by means of any conventional method of solid phase oligonucleotide synthesis, the phosphite triester method using phosphoramidites being the preferred one.

As necessary intermediates for the process of this invention, the new compounds having the general formula (IV), shown above, are also part of this invention. In general formula (IV): B' is the radical of any nucleobase which, in the case of T and U is not protected, and in the case of A, C and G has a standard protecting group on the exocyclic amino group; $R_3$ is a protecting group of the 5'-hydroxyl suitable for the elongation of the chain; $R_2$ is hydrogen or a protecting group of the 3'-terminal phosphate; X is the biradical of a protecting/anchoring group, protecting the 3' terminal phosphate, and simultaneously anchoring (or linking) to the polymeric support; (P') is, either the original polymeric support (P), or a modified polymeric support that additionally has a spacer/bonding group.

The preferred intermediate compounds of formula (IV) are those in which $R_3$ is selected from the group consisting of 4,4'-dimethoxytrityl (DMT), 4-methoxytrityl (MMT) and 9-(9-phenyl)xantenyl (Pix); $R_2$ is selected from the set consisting of hydrogen, methyl (Me), 2-cyanoethyl (CNE), 2-cyano-1,1-dimethylethyl, allyl and p-nitrophenylethyl; biradical X of the protecting/anchoring group is a benzene ring which is linked to the oxygen atom of the 3'-phosphate and to the polymer support (P') through any two of its six carbon atoms, and which is optionally substituted, in any of the four vacant positions, by a radical $R_4$ selected from the group consisting of Cl, Br, $NO_2$ and $OCH_3$; (P') is, either the radical of an original polymeric support (P), or a modified polymeric radical having the formula —$(CH_2)_m$—CO—Y—NH—(P) with m=0–6, preferably with m=1, where Y is either a simple covalent bond or a biradical having the formula —NH—$(CH_2)_s$—CO— with s=1–10, preferably with s=5; the original polymeric support (P) is selected from the group consisting of polystyrene-co-1%-divinylbenzene (PS), polyethyleneglycol-polystyrene copolymer (PEG-PS), polyacrylamide, polystyrene-Kel F, polyethyleneglycol, silica gel, controlled pore glass, cellulose and teflon, the first three being more preferred; and the protecting groups of the nucleobases A, C and G in B' are selected from the group consisting of benzoyl (Bz), isobutyryl (iBu), toluoyl, phenylacetyl, phenoxyacetyl, pivaloyl, dimethylaminomethylene, tert-butylphenoxyacetyl and nitrophenylsulfenyl.

Specially preferred are the above-mentioned intermediate compounds where: $R_2$ is cyanoethyl (CNE), allyl or hydrogen; $R_3$ is 4,4'-dimethoxytrityl (DMT); the protecting groups of A and C in B' are benzoyl (Bz); the protecting group of G in B' is isobutyryl (iBu); the biradical X of the protecting/anchoring group is a benzene ring which is linked to the oxygen of the 3'-phosphate through position 1, which is linked to the polymeric support (P') through position 4, and which is substituted by $R_4$=Cl in position 2; m=1 and s=5 in (P'); and (P) is a polymeric support selected from the group consisting of polystyrene-co-divinylbenzene (PS), polyethyleneglycol-polystyrene (PEG-PS) and polyacrylamide.

Non-anchored intermediates that are necessary for the preparation of (IV) and that are part of this invention, are the new 2-cyanoethyl 3'-(5'-O-dimethoxytrityl)-2'-deoxynucleosidyl 2-chloro-4-(2,4,5-trichlorophenoxycarbonylmethyl)phenyl phosphates of the nucleobases thymine, $N^6$-benzoyladenine, $N^4$-benzoylcytosine and $N^2$isobutyrylguanine B'=T, $A^{Bz}$, $C^{Bz}$, $G^{iBu}$); said non-anchored intermediates having the formula:

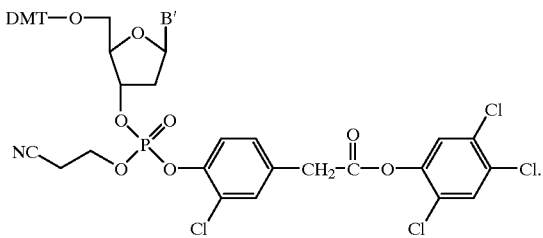

Analogously, the new non-anchored intermediate compounds allyl 3'-(5'-O-dimethoxytrityl)-2'-deoxynucleosidyl 2-chloro-4-(2,4,5-trichlorophenoxycarbonyl-methyl)phenyl phosphates of the nucleobases thymine, $N^6$-benzoyladenine, $N^4$-benzoylcytosine and $N^2$-isobutyrylguanine (B'=T, $A^{Bz}$, $C^{Bz}$, $G^{iBu}$) are also part of this invention; said non-anchored intermediates having the formula:

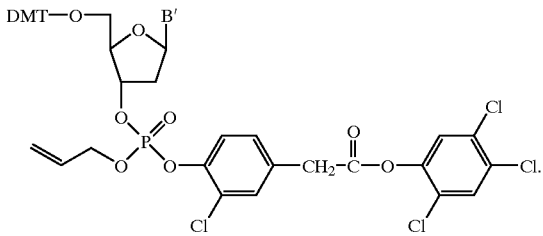

For the preparation of the above-mentioned non-anchored intermediates, the new intermediate compound 2,4,5-trichlorophenyl 3-chloro-4-hydroxyphenylacetate, of formula:

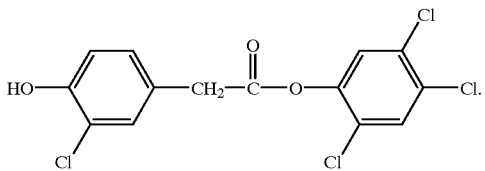

This intermediate is prepared here for the first time, and it is also part of this invention.

An important technical feature of the process of this invention is the requirement that, in order to allow the regioselective formation of a phosphotriester bond in the key step of the cyclization of the linear precursor, the protection scheme must have the highest level of orthogonality, so that the selective deprotection of the 3'-phosphate group involved in the cyclization reaction can be carried out leaving unaltered the protection of the other phosphate groups in the chain. An advantage of the process of this invention lies in the fact that the cyclization reaction takes place on the solid support instead of in solution. This is so because on a solid matrix it is easier to obtain conditions, similar to those of high dilution, which avoid inter-chain reactions that would give rise to the formation of polymers. On the solid support the concentration is very high (about 10 mM) compared with the concentrations used in other cyclization reactions of oligonucleotides, but the polymer is rigid enough to set apart the reactive functions and to minimize the reactions between chains.

The main advantage of the process of this invention, in respect to others known in the art, is that it is of completely general use; that is, it can be used for any type of base and any size of cycle (from 2 to about 50 bases).

Another advantage with respect to other processes proposed in the art, is derived from the fact that, in the process of this invention the known methodology of solid-phase synthesis of oligonucleotides is used together with the phosphite triester method, making the chain elongation simple, rapid and efficient.

On the other hand, the process of this invention makes use of standard protection schemes. This allows the use of commercially available nucleoside derivatives, standard preparation programs and automatic synthesizers. As a consequence of all these features, cyclic structures with synthetic internucleotide linkages, such as methylphosphonates, phosphorothioates and phosphorodithioates, can be obtained. In summary, the process of this invention has the advantage that one can profit from the enormous amount of knowledge and methodologies known for the preparation of analogues of fragments of linear DNA.

Another advantage of the process, associated to the fact that the cyclization reaction is carried out under conditions close to high dilution, is that very few polymers are formed by reaction between the chains.

Moreover, the process of this invention allows an easy scaling-up of the reactions in order to obtain large amounts of cyclic oligonucleotides for structural or biomedical studies.

Finally, the process of this invention solves one of the main difficulties of all methods for the preparation of cyclic oligonucleotides known in the art, namely, the final separation of the desired product from its precursor and from the oligonucleotides and polymers formed during the cyclization reaction. An advantageous feature of the process of this invention, difficult to attain in other cases, is that there is a reaction that discriminates between the cyclic sequences and those which are not cyclic. In the process of the invention this discrimination takes place in the reaction of cleavage of the cyclic oligomer from the resin, where the linear sequences remain attached to the support and are conveniently separated.

DESCRIPTION OF THE PREFERRED EMBODIMENTS

Figure 1:
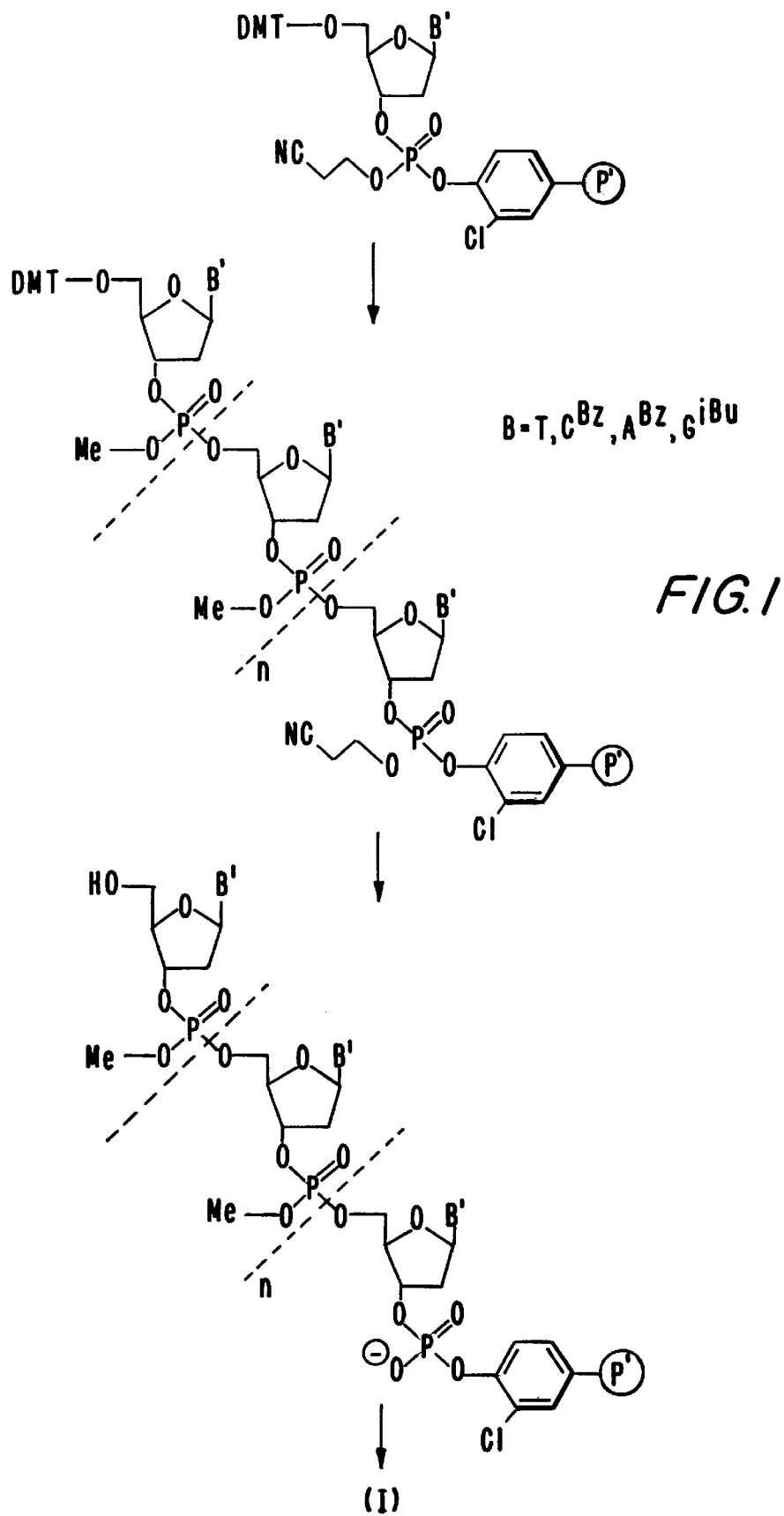
FIG. 1 is a schematic illustration of a preferred preparation process, of a cyclic oligonucleotide (I). In the illustrated case: $R_2$=2-cyanoethyl (CNE), $R_3$=4,4'-dimethoxytrityl (DMT); $R_1$ are all methyl (Me); and the nucleobase protecting groups are: benzoyl (Bz) for cytosine (C) and adenine (A), and isobutyryl (iBu) for guanine (G). The first arrow represents n+1 steps of chain elongation. The second arrow represents the removal of $R_2$ and $R_3$. The third arrow represents cyclization, elimination of the chain phosphate protecting groups, cleavage from the polymer, and elimination of nucleobase protecting groups.

FIG. 1 summarizes a preferred preparation process of this invention, which is illustrated in more detail in the other figures and the accompanying examples. This process is summarized in the following description.

It starts with a protected nucleotide which contains the terminal phosphate group, i.e., the group which has to give rise to the internucleotidic linkage formed in the cyclization step, which is placed at the 3' end of the oligonucleotide and which bears two protecting groups. Protecting group -X-(P') also plays the role of anchor to the solid support, so that it is here called protecting/anchoring group. In the figure -X-(P')=substituted 2-chlorophenyl, is anchored to the solid support through position 4. The other protecting group $R_2$ ($R_2$=2-cyanoethyl in the figure) is eliminated either before starting the chain elongation, or at the end, under conditions in which the protecting groups of the bases and the protecting group -X-(P') remain unaltered. The 5'-hydroxyl group is conveniently protected, by means of the protecting group $R_3$ ($R_3$=DMT in the figure), and can also be eliminated under conditions in which the protecting groups on the bases and the 2-chlorophenyl group remain unaltered. In other words, $R_2$ and $R_3$ are both orthogonal (that is, removable leaving intact) with respect to the protecting groups of the chain and to the protecting/anchoring group -X-(P'). Among the nucleobases, thymine (T) and uracyl (U) are left unprotected, whereas the others are adequately protected. In particular, in the figure the following protecting groups are used: benzoyl (Bz) for cytosine (C) and adenine (A), and isobutyryl (iBu) for guanine (G).

In the figures and formulae of this specification, (P) represents a radical of the polymeric support, and (P') a radical of the polymeric support which includes also a spacer and/or a linker to the benzene ring of the protecting/anchoring group X.

The first arrow of FIG. 1 represents the elongation sequence of the oligonucleotide chain, of a desired number of times n, which is an integer number greater or equal to zero. The elongation takes place by subsequent reactions of conventional type, but using phosphate protecting groups $R_1$ ($R_1$=Me in the figure) which remain unaltered during the separation of the protecting group 2-cyanoethyl and of the protecting group DMT.

The second arrow in FIG. 1 represents the deprotection of the $3^1$-phosphate of the starting nucleotide, if it has not been previously removed, as well as the deprotection of the 5'-hydroxyl protecting group of the last nucleotide added to the chain. Both deprotections can be carried out in any order.

The last arrow in FIG. 1 represents the set of four reactions: a) the cyclization, i.e. the formation of the internucleotide linkage between the 3'-phosphate group and the 5'-hydroxyl group; b) the elimination of the protecting groups of the phosphates of the chain (Me in the figure); c) the cleavage from the polymer, by elimination of the substituted 2-chlorophenyl protecting group in the figure; and d) the elimination of the nucleobase protecting groups. The last three reactions can be carried out simultaneously or sequentially (in any order).

The different steps of this particular embodiment of the process of the invention are described below in more detail.

a) Anchoring of the 3' Terminal Nucleotide to the Polymeric Support

Figure 2:
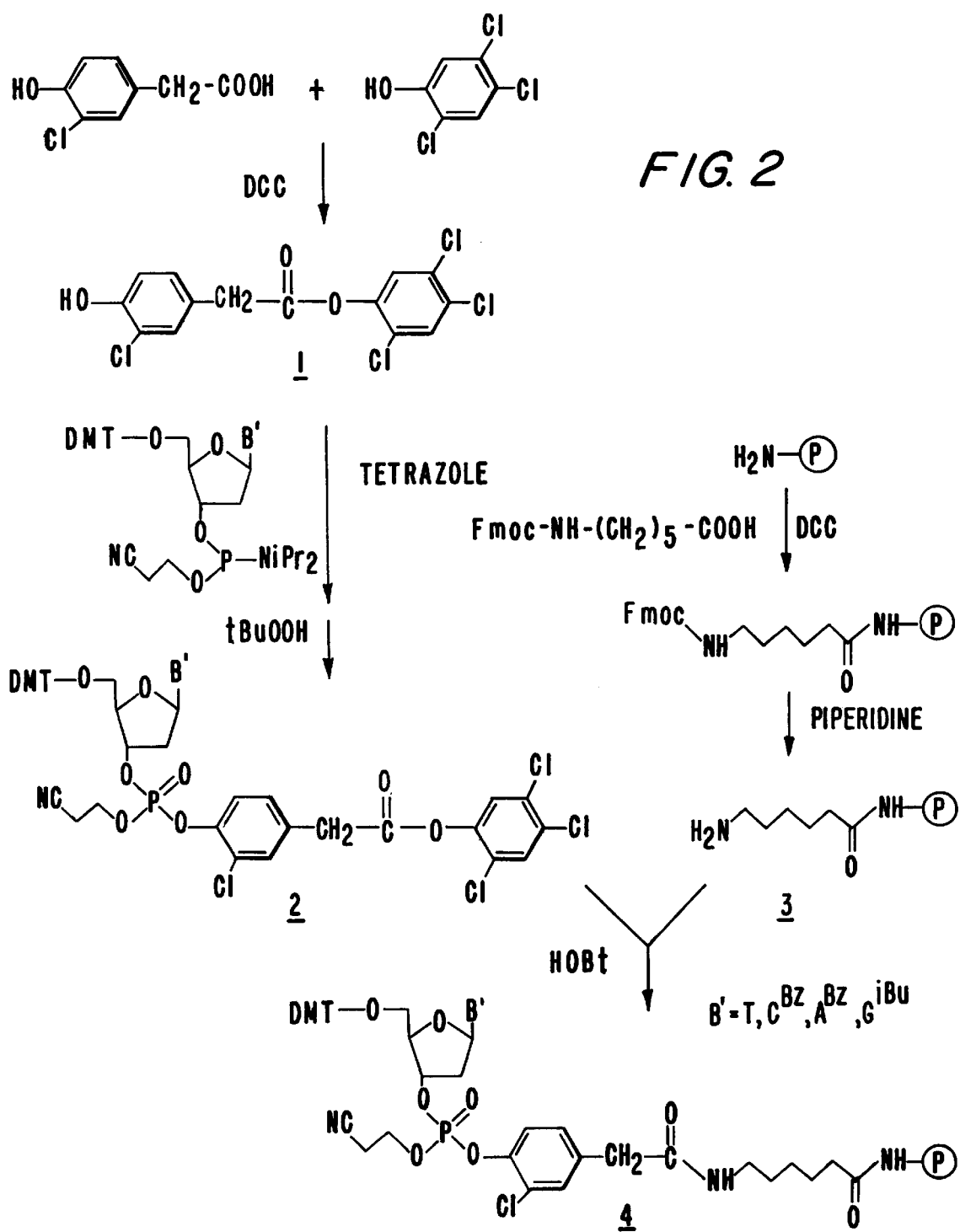
FIG. 2 is a schematic illustration of the preparation process of the anchored and protected nucleotide used as starting material in FIGS. 3 and 4. The polymeric support has an 6-aminohexanoic acid spacer and the nucleotide is anchored through a 3-chloro-4-hydroxyphenylacetic acid linker.

The preferred polymeric supports (P) in the process of this invention are, either of the type polystyrene-co-1%-divinylbenzene (PS), or of the type polyethyleneglycol-polystyrene copolymer (PEG-PS), all of them compatible with the phosphite triester method and useful for the large scale synthesis. As illustrated in FIG. 2, the polymeric support (P) is preferably functionalized with amine groups to yield the functionalized support represented as (P)-$NH_2$. It is even more preferable to introduce a spacer between the polymer and the amine group to which the first nucleotide is anchored, in order to separate from the support the 3' end of the oligonucleotide and to make it more accessible during the key cyclization step. Moreover, the spacer permits limitation of the substitution degree of the starting polymer that, particularly in the case of polystyrene, is often too high for the preparation of oligonucleotides. In FIG. 2 a linear chain of 6 carbon atoms has been introduced, but this chain could be longer or shorter. FIG. 2 illustrates the anchoring of the 3' terminal nucleotide to the polymeric support through a 3-chloro-4-hydroxyphenylacetic acid bifunctional spacer or linker. To obtain the nucleotide-linker-polymer it is convenient to synthesize in solution the nucleotide-linker as phosphate triester, in order to facilitate its purification and characterization; this is preferable to the alternative way of carrying out all the reactions on a solid matrix and incorporate the nucleoside phosphoramidite onto the result of the linker-polymer union. For this purpose, the carboxylic acid of the linker is protected as 2,4,5-trichlorophenyl ester, thus being at the same time activated for the reaction of incorporation onto the amine groups on the polymer. Product (1), the four protected nucleotides (2), and the four anchored and protected nucleotides (4) of FIG. 2 are products not described before.

b) Optional Removal of the CNE Group Before the Chain Elongation

Figure 3:
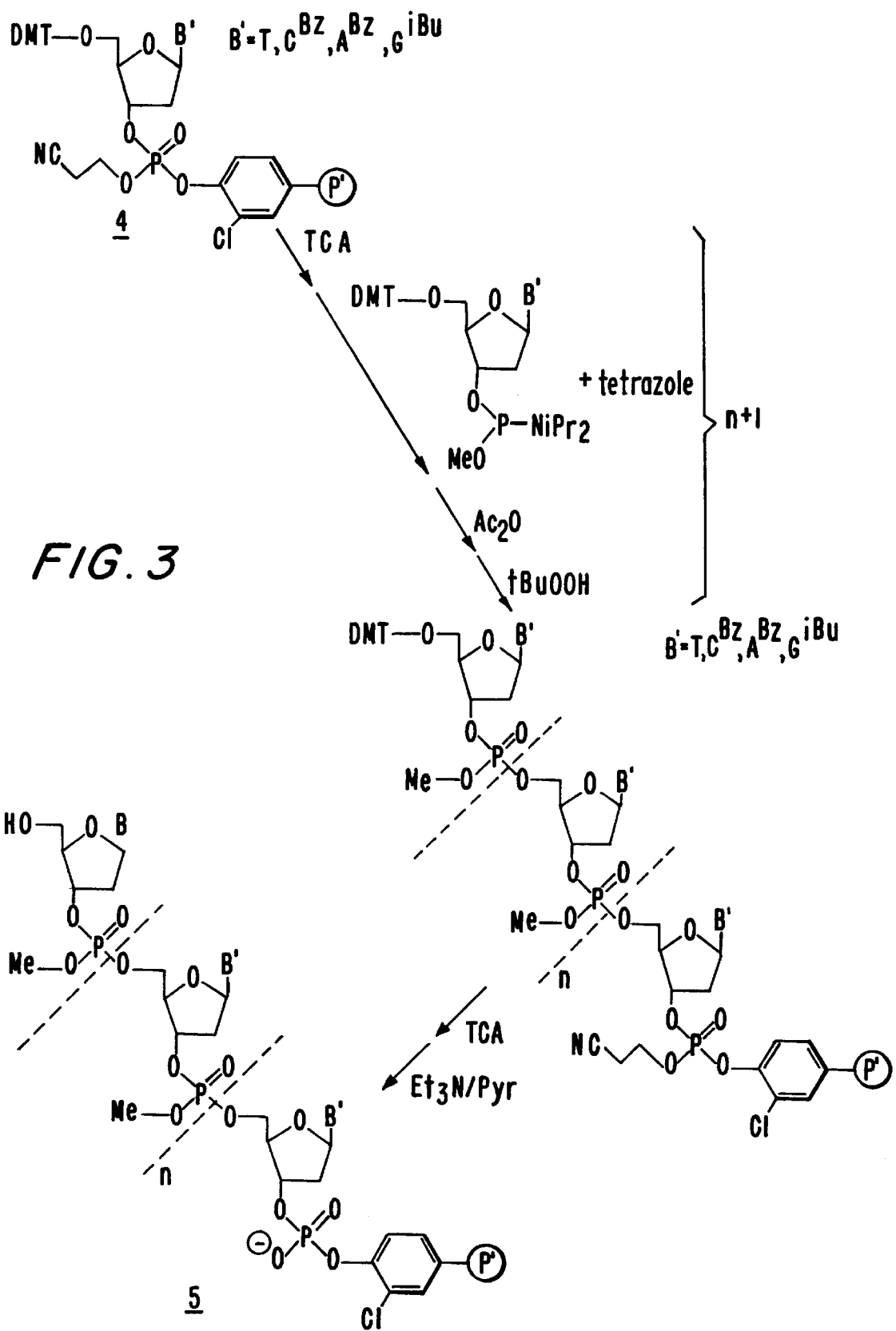
FIG. 3 is a schematic illustration of the elongation of the oligonucleotide chain (set of several arrows), in a case in which the 2-cyanoethyl (CNE) protecting group is being maintained. The last two arrows illustrate the removal of DMT and CNE protecting groups.
Figure 4:
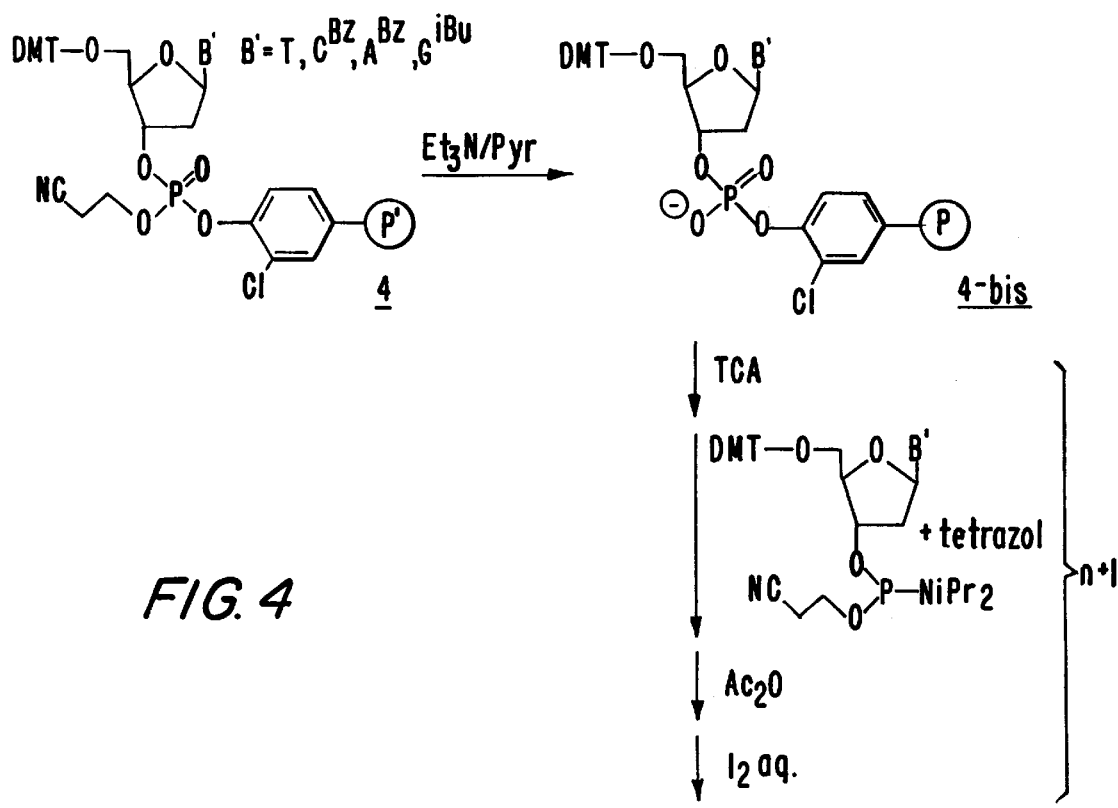
FIG. 4 is a schematic illustration of the elongation of the oligonucleotide chain (set of several arrows), in a case in which the 2-cyanoethyl (CNE) protecting group has been eliminated before (first arrow). The last arrow illustrate the elimination of DMT protecting group.
Figure 4:
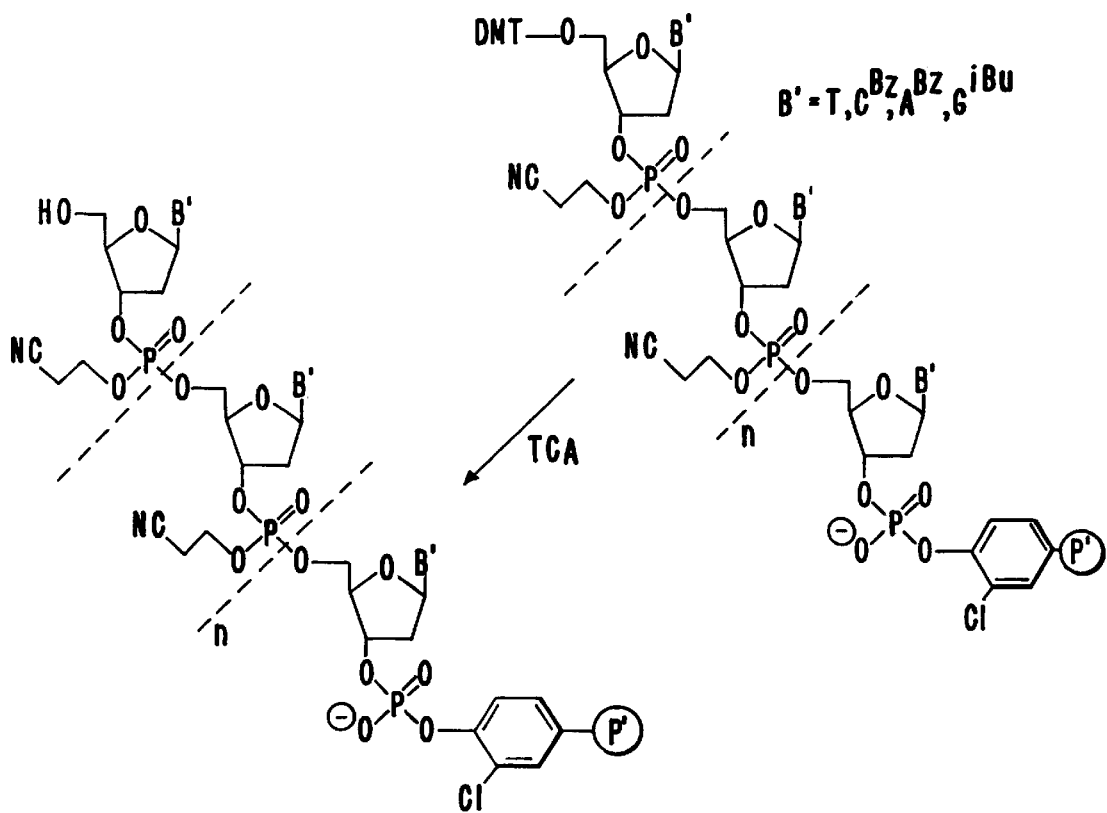

The protecting group 2-cyanoethyl of the four protected and anchored nucleotides (4) of the FIG. 2 is either maintained (as in FIG. 3) or removed with triethylamine/pyridine before the chain elongation (as in FIG. 4).

c) Elongation on the Polymer Support

The sequential elongation of the oligonucleotide chain is carried out starting with the protected and anchored nucleotide (4), or alternatively with the product obtained after removing the 2-cyanoethyl group, and proceeding in the conventional way for the solid phase synthesis of oligonucleotides, making use of 3'-methyl-N,N-diisopropylphosphoramidite derivatives of 5'-dimethoxytrityl-nucleosides (B=T, $C^{Bz}$, $A^{Bz}G^{iBu}$) as shown in FIG. 3. The reactions can be carried out in an automatic synthesizer and on any support, although polystyrene, polyethylleneglycol-polystyrene and polyacrylamide supports are preferred. Average coupling yields of phosphoramidites are similar to those obtained in any preparation of DNA fragments on the same supports or on CPG (97–98%). The new oligonucleotide-resin union is completely stable under the conditions of the preparation (deprotection, coupling, capping and oxidation). Once the preparation of the linear oligonucleotide is finished, the 5'-hydroxyl group is deprotected with trichloroacetic acid (TCA) and the cyanoethyl group (CNE) is eliminated (if it has not been previously removed) by means of a treatment with triethylamine/pyridine. The linear, protected and anchored oligonucleotide (5) is thus obtained.

FIG. 4 illustrates a case in which the protecting group $R_2$ has been removed before chain elongation, and where all the protecting groups of the phosphates of the chain are 2-cyanoethyl. (4-bis) is a new product, both in its protonated and its ionic form.

d) Cyclization, Deprotection and Cleavage From the Solid Support

Figure 5:
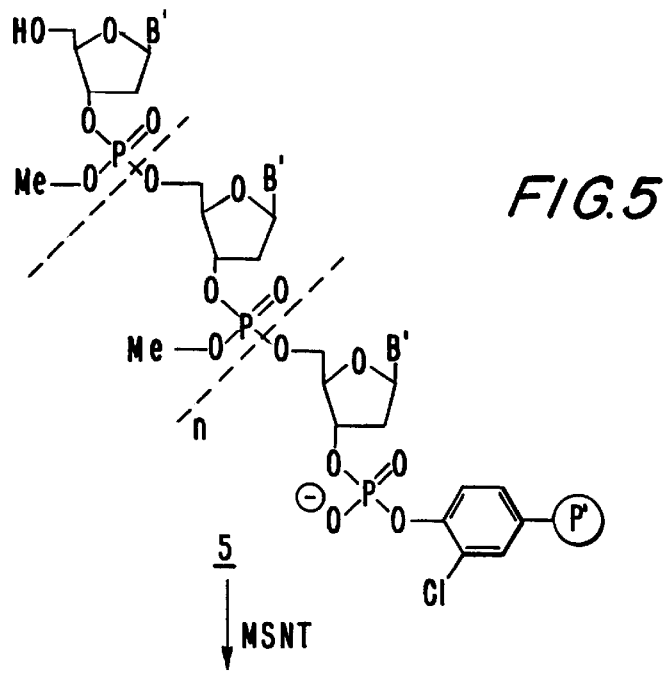
FIG. 5 is a schematic illustration of the transformation of the anchored chain obtained in FIG. 3 into a cyclic oligonucleotide (I). The first arrow represents the key cyclization step. The last three arrows represent, respectively, the deprotection of the phosphate groups, the cleavage from the resin, and the deprotection of the nucleobases.
Figure 5:
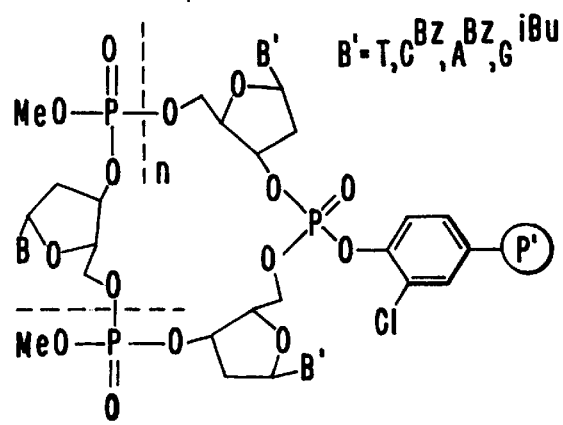
Figure 5:
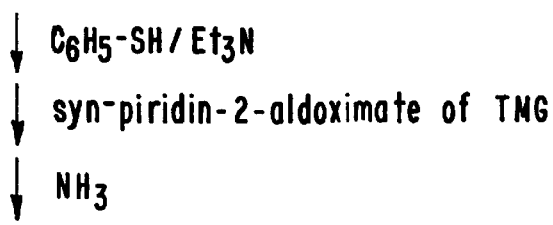
Figure 5:
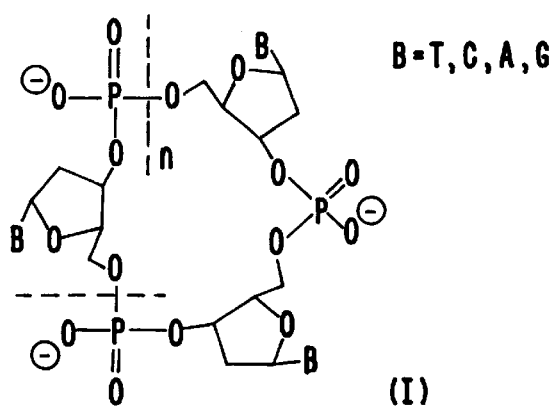

FIG. 5 shows a particular case of the key cyclization step between the 3'-terminal phosphate diester and the 5'-hydroxyl group that is carried out with 1-mesitylenesulfonyl-1,2,4-triazole in the presence of pyridine. After the formation of the cyclic oligonucleotide, which remains anchored to the polymeric support through a phosphate triester bond, the other phosphate protecting groups are deprotected by a treatment with thiophenol and triethylamine. The separation of the cyclic oligomer from the resin is carried out by reaction with tetramethylguanidinium syn-pyridin-2-aldoximate in dioxane/water. And, finally, the protecting groups of the nucleobases are eliminated by treatment of the cyclic oligonucleotide with ammonia. The desired cyclic oligonucleotide (I) is thus obtained, where B now means any radical of any unprotected nucleobase.

Figure 6:
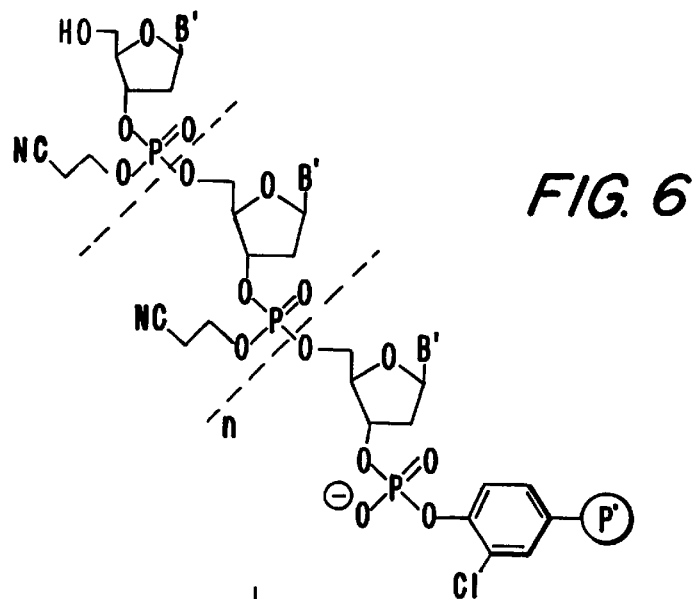
FIG. 6 is a schematic illustration of the reactions analogous to those of FIG. 5, but starting with an anchored chain in which all chain phosphate protecting groups are 2-cyanoethyl, such as the chain prepared in FIG. 4.
Figure 6:
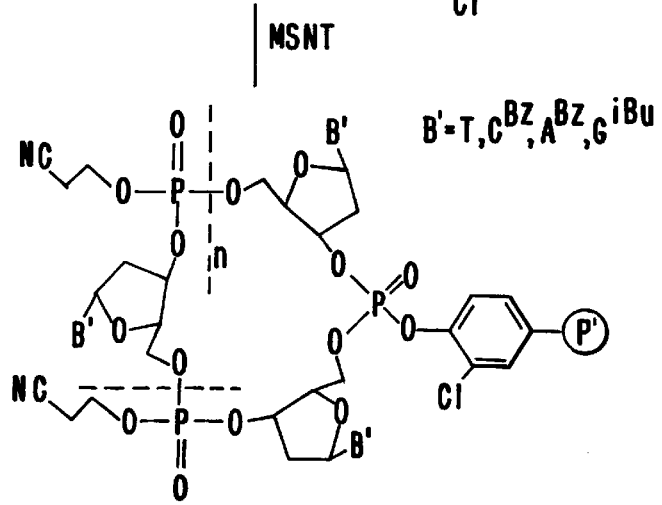
Figure 6:
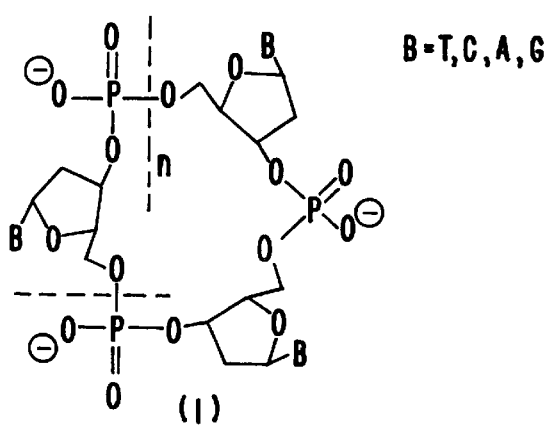

FIG. 6 shows another particular case of the key cyclization step where all the protecting groups of the phosphates of the chain are 2-cyanoethyl (such as the product obtained by the chemical elongation shown in FIG. 4).

e) Purification and Characterization of the Cyclic Oligonucleotides

After gel filtration chromatography through Sephadex G-10 to separate the oximate and other by-products of low molecular weight, the cyclic oligonucleotide is analyzed by high-performance liquid chromatography (HPLC) using a stationary octadecyl-silica reversed phase ($C_{18}$-HPLC) and purified with the same chromatographic system or, alternatively, by ion-exchange chromatography through DEAE-Sephadex. The retention time of the cyclic oligonucleotide in reversed phase HPLC must be different from the retention time, under the same conditions, of the oligonucleotide 3'-phosphate with the same nucleotide sequence that would be obtained if the cyclization reaction did not take place. In order to verify this point the linear oligonucleotide-3'-phosphates can be synthesized using a polymeric support with a 2-(2-nitrophenyl)ethyl linker (NPE resin), and this has been performed in some cases. The cyclic nature of the synthesized oligonucleotides can be demonstrated by reversed phase HPLC analysis of the products obtained after enzymatic digestion. It was shown that the enzymatic digestion with snake venom phosphodiesterase and alkaline phosphatase of cyclic oligonucleotides yields the expected nucleosides with the correct relative proportion, whereas the cyclic oligonucleotides are not digested by calf spleen phosphodiesterase. Finally, mass spectrometry (negative electrospray) of cyclic oligonucleotides (when they are obtained in sufficient amount) gives the final proof of structure: nucleotide composition and cyclic character.

The present invention is further illustrated with the following non-limiting examples.

EXAMPLE 1

Preparation of 2,4,5-trichlorophenyl 3-chloro-4-hydroxyphenylacetate (1)

A solution of 4 g (21.6 mmol) of 3-chloro-4-hydroxyphenylacetic acid in 130 mL of ethyl acetate is slowly added to a solution of 4.7 g (23.6 mmol) of 2,4,5-trichlorophenol and 4.9 g (23.6 mmol) of DCC in 22 mL of dichloromethane and the reaction mixture is stirred overnight. The precipitate formed is separated by filtration and the solution is chilled to precipitate the rest of N,N-dicyclohexylurea. After a second filtration, the filtrate is washed three times with a solution of sodium bicarbonate, dried over $MgSO_4$ and evaporated to dryness in a rotary evaporator. The resulting oil is chromatographed through silica gel eluting with hexanes and increasing amounts of dichloromethane. The desired product appears in the fraction eluted with 50% dichloromethane. After elimination of the solvent 2.8 g of product are isolated (34% yield), with the following analytical data: mp=77° C. Rf=0.33 (AcOEt/hexanes 3:7).

$^1$H-NMR (200 MHz, $CDCl_3$): 7.5 (1H, s, $Cl_3Ar$), 7.35 (1H, d, ClAr), 7.26 (1H, s, $Cl_3Ar$), 7.20 (1H, dd, ClAr), 7.03 (1H, d, ClAr), 5.6 (1H, s, OH), 3.82 (2H, s, $CH_2$). MS (EI): M=366.

EXAMPLE 2

Preparation of 2-cyanoethyl 3'-(5'-O-dimethoxytrityl)-2'-deoxynucleosidyl 2-chloro-4-(2, 4 5-trichlorophenoxycarbonylmethyl)phenyl Phosphates of the Four Protected Nucleobases (2)

General process: 16 mg of tetrazole (0.23 mmol) in 0.7 mL of acetonitrile are added to a solution of 0.23 mmol 5'-O-dimethoxytrityl-2'-nucleoside 3'-O-(2-cyanoethyl)-N, N-diisopropylphosphor-amidite (B=T, $C^{Bz}$, $A^{Bz}$, $G^{iBu}$) and 81 mg (0.21 mmol) of 2,4,5-trichlorophenyl 3-chloro-4-hydroxyphenylacetate (1) in 1.7 mL of dichloromethane under argon atmosphere. After one hour, 0.24 mL of a 3 M solution of tert-butylhydroperoxide in toluene are added. 10 min later the reaction mixture is washed with water and the organic phase is dried over $Na_2SO_4$, concentrated in the rotary evaporator to a volume of 1 mL and poured onto 40 mL of hexanes to precipitate the product. After centrifugation and elimination of the hexanes, the product is dried in a desicrator, to yield a white solid as a foam. The analytical data corresponding to the products derived from the four protected nucleobases are the following:

Thymidine. Yield 75%. Rf=0.33 (CH$_2$Cl$_2$/MeOH 95:5). $^{31}$P-NMR (CDCl$_3$): −8.48 ppm. N$^4$-benzoylcytidine. Yield 73%. Rf=0.3 (CH$_2$Cl$_2$/MeOH 70:30). $^{31}$P-NMR (CDCl$_3$): −8.50 ppm. N$^6$-benzoyl-adenosine. Yield 66%. Rf=0.3 (CH$_2$Cl$_2$/MeOH 95:5) $^{31}$P-NMR(CDCl$_3$): −8.55, −8.72 ppm N$^2$-isobutyryl-guanosine. Yield 65%. Rf=0.4 (CH$_2$Cl$_2$/MeOH 95:5) $^{31}$P-NMR (CDCl$_3$): −8.51 ppm.

EXAMPLE 3

Preparation of Resin (3)

In a 10 mL-syringe equipped with a polypropylene disk are introduced 1.5 g of aminomethylpolystyrene (Sigma, 0.81 mmol NH$_2$/g of resin), 44.6 mg (0.24 equiv.) of 1-hydroxybenzotriazole in 0.8 mL of DMF, 63.2 mg (0.24 equiv.) of DCC in 2 mL of DCM and 103 mg (0.24 equiv.) of N-Fmoc-6-aminohexanoic acid in 5 mL of DCM and 0.4 mL of DMF and left to react, with occasional stirring, for two hours. The resin is washed with DMF (3×1 min), DCM (3×1 min) and MeOH (3×1 min), dried and the functionalization is determined on an aliquot. The remaining amine groups are acetylated with acetic anhydride (100 equiv.) in DMF for 10 min, after which time DIEA (10 equiv.) is added and left to react for 10 min more, and the resin is washed again. The absence of free amine groups is confirmed by the ninhydrin test. In order to eliminate the Fmoc group, and at the same time determine the degree of substitution, the resin is treated with a solution of 50% piperidine in DMF (3×2 min) and washed with DCM (3×1 min), DMF and MeOH. The filtrates from the treatment with piperidine and DCM washes are pooled and the amount of N-(9-fluorenylmethyl) piperidine formed in the deprotection determined spectrophotometrically (lambda=300 nm, epsilon=7800). Resins with a substitution degree between 0.05 and 0.1 mmol NH$_2$/g resin are obtained.

EXAMPLE 4

Anchoring of the 3'-Terminal Nucleotide to the Resin. Preparation of Reagent (4)

In a 10 ml-syringe equipped with a polypropylene disk, 200 mg of resin (3) (approx. 0.014 mmol NH$_2$) are treated with 29 mg (0.028 mmol) of nucleoside derivative (2) (B=T), 4.3 mg (0.028 mmol) of HOBt and 5.8 mg (0.028 mmol) of DCC in 2 mL of DCM/DMF (4:1). The suspension is mechanically stirred for two hours. At the end of the reaction the resin is washed with DCM, DMF and MeOH (3×1 min of each solvent), dried and the functionalization is determined. If the value obtained is not satisfactory the reaction is repeated under the same conditions.

The substitution degree is determined by treating an aliquot of the resin with a 3% solution of trichloroacetic acid in DCM and spectrophotometrically quantifying the dimethoxytrityl cations (lambda=498 nm, epsilon=71700) formed in the deprotection reaction. A substitution degree of 0.057 mmol DMT/g of resin is obtained.

Previous to the oligonucleotide preparation, the remaining amine groups are acetylated as described in the preparation of resin (3).

EXAMPLE 5

Removal of the Protecting Group 2-cyanoethyl of the 3'-Terminal Phosphate. Preparation of Reagent (4-bis)

In a 10 mL syringe equipped with a polypropylene disk, 200 mg of resin (4) are treated with triethylamine/pyridine (1:1) for 3 hours. The resin is washed with pyridine, DCM and MeOH and dried under argon atmosphere. The resin (4-bis) is obtained with a quantitative yield.

EXAMPLE 6

Solid Phase Preparation of Linear Oligonucleotide (5)

The preparations are carried out in a 380B ABI automatic synthesizer starting with a resin functionalized with the 3' terminal nucleotide and usually at the 1 μmol scale. For the subsequent elongation of the chain 5'-O-dimethoxytrityl-2'-deoxynucleoside 3'-O-methyl-N,N-diisopropylphosphoramidites (B=T, C$^{Bz}$, A$^{Bz}$, G$^{iBu}$) are used. The protocol for the cycle of incorporation of a nucleotide is the following:

| Step | Reagent or solvent | Time(s) |
|---|---|---|
| 1 | DCM | 1 × 20 |
| 2 | 3% TCA/DCM | 3 × 30 |
| 3 | DCM | 2 × 20 |
| 4 | 5% DIEA/DCM | 1 × 30 |
| 5 | DCM | 2 × 20 |
| 6 | ACN | 1 × 45 |
| 7 | Dry with argon | 1 × 45 |
| 8 | 0.1M phosphoramidite in DCM + 0.5M tetrazole in THF | 15 min |
| 9 | THF | 1 × 30 |
| 10 | Ac$_2$O/2,6-lutidine/THF (1:1:8) + 17.6% NMI in THF | 2 min |
| 11 | DCM | 1 × 45 |
| 12 | 0.1M I$_2$ in pyridine/THF/H$_2$O (20:80:2) or 1M tBuOOH in toluene/DCM (1:2) | 1 min |
| 13 | THF | 1 × 60 |
| 14 | DMF | 1 × 60 |
| 15 | DCM | 2 × 20 |

The average coupling yields of the phosphoramidites are of 97–98%, as determined by spectrophotometric analysis of the trityl cations formed at every deprotection step.

When the preparation of the oligonucleotide chain is finished, in the same automatic synthesizer or in a syringe equipped with a filtering disk, the DMT of the 5'-hydroxyl is eliminated by repeating the first three steps of the synthesis cycle. Then the cyanoethyl group (if it has not been previously removed) is eliminated by treatment with Et$_3$N/pyridine (1:1) for one hour. The resin is washed with pyridine, DCM and MeOH and dried under argon atmosphere.

EXAMPLE 7

Cyclization, Deprotection and Cleavage. Preparation of Cyclic Oligonucleotide (I)

The linear oligonucleotide anchored to the resin (5) is cyclized by treatment with a 0.1 M solution of mesitylenesulfonyl-3-nitro-1,2,4-triazole in pyridine for 24 hours. Sometimes, two treatments are carried out amounting to the same total time, inserting washes of the resin with pyridine.

The resin is washed with DCM and dioxane and, then, is treated twice for 30 min with a solution of thiophenol/Et$_3$N/dioxane (1:2:2). At the end the resin is washed again with dioxane, DCM and methanol.

In order to cleave the oligonucleotide from the resin, this is treated with a 0.1 M solution of N,N,N',N'-tetramethylguanidinium syn-pyridine-2-aldoximate in dioxane/water (2:1) for different periods of time, amounting to 24 hours, and inserting dioxane/water washes. The filtrates from the different treatments with oximate are pooled and the solvent is eliminated. The residue is treated with a 33% aqueous ammonia solution for 16 hours at 55° C. After elimination of the ammonia, the product is chromatographed through a Sephadex G-10 column, eluting with 0.05 M triethylammonium bicarbonate buffer and following the elution profile at 260 nm. The fractions eluted at the beginning, which contain the cyclic oligonucleotide, are pooled and lyophilized twice.

EXAMPLE 8

Analysis and Purification of Cyclic Oligonucleotide (I)

The cyclic oligonucleotides are analyzed by high performance column chromatography on a stationary phase of octadecyl-silica (4.6×250 mm column, 10 μm particle size) and eluting with a gradient of 0.01 M solution of triethylammonium acetate (TEAA) in water and acetonitrile (A=0.01 M TEAA in water, B=acetonitrile/water 1:1, gradient from 0% to 60% of B in 20–30 min, 1 mL/min). The elution is followed at 260 nm.

The purification of the products can be carried out using the same chromatographic system or, alternatively, by ion-exchange chromatography on DEAE-Sephadex eluting with a gradient of triethylammonium bicarbonate.

EXAMPLE 9

Characterization of Cyclic Oligonucleotides (I)

a) Enzymatic Digestion with Calf Spleen Phosphodiesterase

A small aliquot of the cyclic oligonucleotide (approx. 0.5 $OD_{260}$) is treated at 37° C. for 16 hours with the following mixture: 30 μL of calf spleen phosphodiesterase solution (E.C. 3.1.16.1, Sigma), and 118 μL of buffer solution. The buffer solution is prepared with: 500 μL of 0.1 M Tris.HCl, pH 8; 100 μL Of 0.1 M $MgCl_2$ ; and 400 μL of water.

b) Enzymatic Digestion with Snake Venom Phosphodiesterase and Alkaline Phosphatase.

The same amount of cyclic oligonucleotide is treated (37° C. , 16 h) with: 1 μg of snake venom phosphodiesterase (E.C. 3.1.4.1, Sigma); 2 μL of alkaline phosphatase solution (E.C. 3.1.3.1, Sigma); and 118 μL of buffer solution.

c) HPLC Analysis of the Products of Enzymatic Digestion.

The products of the enzymatic digestions are analyzed by $C_{18}$ reversed phase HPLC using the same eluent system as for the analysis of the oligonucleotides : 4.6×250 mm column, 10 μm particle size, gradient from 0 to 60% of B in 20 min, flow rate 1 mL/min, detection 260 nm. In order to identify the peaks of the chromatogram, samples of the different nucleosides are analyzed separately. The integration of the area of the peaks resulting from the analysis allows to determine the relative proportion of the 2'-deoxyribonucleosides on the basis of their relative absorptivity values.

d) Mass Spectrometry. Spectra Obtained with a VG Apparatus from Fisons Instruments.

EXAMPLE 10

Preparation of Specific Cyclic Oligonucleotides (I)

Following the general processes described above the following cyclic oligonucleotides have been prepared:

a) Oligonucleotide $c(T_3)$

It is synthesized on the 1 μmol scale on a polystyrene resin with a starting functionalization of 4 (B=T) of 57 μmol DMT/g resin. The final deprotection treatment with ammonia is omitted provided that thymidine does not require protection. The overall preparation yield (preparation, cyclization, deprotection and cleavage) of the cyclic oligomer is 29%. $c(T_3)$ elutes in analytical HPLC with a retention time of 11.6 min (gradient from 0 to 40% of B in 20 min). The enzymatic digestion of the product with snake venom phosphodiesterase and alkaline phosphatase yields thymidine only, while the oligonucleotide remains unaltered to the treatment with calf spleen phosphodiesterase. The mass spectrum (negative electrospray) of the cyclic oligonucleotide affords signals at m/z 911.5 $(M—H)^-$, 455.3 $(M-2H)^{2-}$ and 303.1 $(M-3H)^{3-}$. For an expected mass of 912.13, the mass found is 912.5.

b) Oligonucleotide $c(T_6)$

It is synthesized on the 1 μmol scale on a polystyrene resin with a starting functionalization of (4) (B=T) of 57 μmol DMT/g resin. The final deprotection treatment with ammonia is omitted provided that thymidine does not require protection. The overall synthesis yield of the linear oligonucleotide (5) is 91%. The overall preparation yield (preparation, cyclization, deprotection and cleavage) of the cyclic oligomer is 27%. The HPLC purification yield is 48%. $c(T_6)$ elutes in analytical HPLC with a retention time of 13.3 min (gradient from 0 to 60% of B in 20 min). Under the same chromatographic conditions the linear oligonucleotide 3'-phosphate ($^{5'}TpTpTpTpTpTp^{3'}$) has a retention time of 12.2 min. The enzymatic digestion of the product with snake venom phosphodiesterase and alkaline phosphatase yields thymidine only, while the oligonucleotide remains unaltered to the treatment with calf spleen phosphodiesterase.

c) Oligonucleotide $c(d^{5'}CATTCATT^{3'})$ c1) Synthesized at the 1 μmol scale on a polystyrene resin with a starting functionalization of (4) (B=T) of 53 μmol DMT/g resin. The overall synthesis yield of the linear oligonucleotide (5) with the sequence TCATTCAT-resin is 95%. The overall preparation yield (preparation, cyclization, deprotection and cleavage) of the cyclic oligomer is 17%. c(CATTCATT) elutes in analytical HPLC with a retention time of 11.4 min (gradient from 10 to 40% of B in 20 min). Under the same chromatographic conditions the linear oligonucleotide 3'-phosphate ($^{5'}TpCpApTpTpCpApTp^{3'}$) elutes at 11.9 min. The HPLC analysis of the enzymatic digestion of the oligonucleotide with snake venom phosphodiesterase and alkaline phosphatase yields the expected 2'-deoxynucleosides with the correct relative proportion (dC:1, T:2.03, dA:1), while the oligonucleotide remains unaltered to the treatment with calf spleen phosphodiesterase.

c2) The preparation of this product has also been carried out at a 7.4 μmol scale on a polyethyleneglycol-polystyrene support with a substitution degree of (4) (B=T) of 69 μmol DMT/g resin. The overall preparation yield of the linear oligonucleotide was 94% and the overall preparation yield of the cyclic oligonucleotide (preparation, cyclization, deprotection and cleavage) of 20%. The crude preparation product, which shows a degree of purity of 97% by HPLC, was purified by chromatography through DEAE-Sephadex (gradient from 0.1 M to 1.2 M TEAB, pH 7, 1.2 mL/min), to yield a completely homogeneous product and completely indistinguishable from the cyclic octamer synthesized on the polystyrene support. The mass spectrum (negative electrospray, injection of 10 μL of a solution in $MeOH/H_2O$ (1:1) containing 0.5 OD$_{260}$) of the cyclic oligonucleotide gives signals at m/z 604.44 (M—4H)$^{4-}$ and 806.15 (M-3H)$^{3-}$. For an expected mass of 2421.55, the mass found is 2421.63.

c3) The same product has also been prepared at 10 mmol scale on a polyethyleneglycol-polystyrene support with a substitution degree of (4) (B=T) of 74 μmol DMT/g resin. Before chain elongation the 2-cyanoethyl group has been removed with a Et$_3$N/Pyr treatment for three hours. The overall preparation yield of the linear oligonucleotide, using the 2-cyanoethylphosphoramidites of the nucleosides, has been 94%. After the cyclization, the deprotection is carried out replacing the treatment with thiophenol/triethylamine by a three hours treatment with Et$_3$N/Pyr. The overall synthesis yield of the cyclic oligonucleotide (preparation, cyclization, deprotection and cleavage) has been 41%. The crude product, having a degree of purity by HPLC of 85%, has been purified by ion exchange chromatography as above. A product completely homogeneous and indistinguishable from the cyclic octamer synthesized by the methods described above has been obtained.

d) Oligonucleotide c(d$^{5'}$TTCACATTTTCACATT$^{3'}$) (SEQ. ID. No.: )

It is synthesized on the 1 μmol scale on a polystyrene resin with a starting functionalization of (4) (B=T) of 57 μmol DMT/g resin. The overall preparation, cyclization, deprotection and cleavage yield has been of 21% and the product is obtained with a degree of purity by HPLC of 88%. The cyclic hexadecamer is eluted in analytical HPLC with a retention time of 9.0 min (gradient from 0 to 60% of B in 10 min, followed by isocratic 60% of B for 5 min). The linear oligonucleotide 3'-phosphate is eluted in HPLC with a retention time slightly lower that the cyclic oligonucleotide. The enzymatic digestion with snake venom phosphodiesterase and alkaline phosphatase of the cyclic oligonucleotide, followed by HPLC analysis of the resulting nucleosides yields the expected 2'-deoxynucleosides with the relative proportion dC:1.04, T:1.93 and dA:1.02, as compared with the expected values dC:1; T:2 and dA:1.

What is claimed is:

1. A process for preparation of a single stranded cyclic oligonucleotide of formula (I), or a salt or solvate thereof, by solid phase synthesis

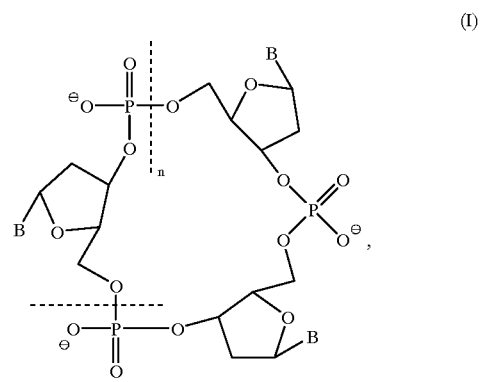

(I)

wherein the B groups in the oligonucleotide of formula I are the same or different from each other and each B is selected from the group consisting of endocyclic nitrogen radicals of nucleobases, each of said nucleobases being selected from the group consisting of thymine, uracil, adenine, cytosine and guanine (T, U, A, C or G); the oligonucleotide of formula I has a plurality of furanose groups with 3'-hydroxy groups and 5'-hydroxy groups which are the same or different from each other, are substituted at said 3'-hydroxy groups and 5'-hydroxy groups, and are biradicals of D-2-deoxyribofuranose or biradicals of D-ribofuranose; and n is an integer between 0 and about 50; said process comprising the steps of:

a) protecting and anchoring a nucleotide of formula (IV) having a 3'-terminal phosphate group and a 5'-hydroxy group to a polymeric support via said phosphate group,

---

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: OLIGONUCLEOTIDE

<400> SEQUENCE: 1
ttcacatttt cacatt                    16

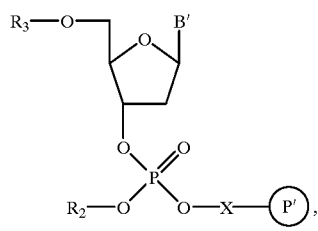

(IV)

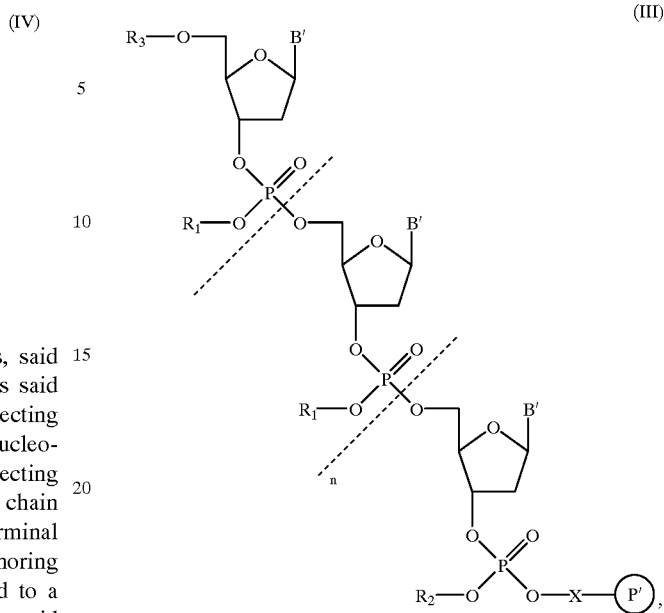

(III)

wherein B' is a radical of one of said nucleobases, said radical not being protected when said nucleobase is said thymine or said uracil, and being protected with a protecting group bound to an exocyclic amine group when said nucleobase is said adenine, cytosine or guanine; $R_3$ is a protecting group of the 5'-hydroxy group and is structured for chain elongation; $R_2$ is a protecting group bound to the 3'-terminal phosphate group; X is a biradical consisting of an anchoring group bound to the 3'-terminal phosphate group and to a polymeric support (P) to protect as well as anchor said phosphate group to the polymeric support (P) and P' is a radical of said polymeric support (P) or a radical of a modified polymeric support including a spacer/bonding group;

b) after the protecting and anchoring of the nucleotide of formula (IV) in step a), removing the protecting group $R_2$ of the 3'-terminal phosphate group;

c) performing a chain elongation consisting of a sequence of n+1 chain elongation steps using a nucleotide having a predetermined one of said nucleobases in each of said chain elongation steps; wherein said nucleotides used in said chain elongation steps each have 5'-hydroxy groups and a 3'-phosphate group and protecting groups $R_3$ bound to said 5'-hydroxy groups to protect said 5'-hydroxy groups; said protecting groups $R_3$ are equal or different from each other and structured for said chain elongation; said nucleotides used in each of said chain elongation steps are protected at said 3'-phosphate group with a chain phosphate protecting group $R_1$, said chain phosphate protecting groups $R_1$ are the same or different from each other, and are selected so that $R_2$ and $R_3$ are removable under conditions in which a bond between the anchoring group X and P', the protecting group $R_1$ and the protecting groups of said adenine, cytosine or guanine in said B' remain unaltered; so that a protected and anchored intermediate oligonucleotide of the formula (III) is obtained;

d) removing said protecting group $R_3$ and said protecting group $R_2$ of the anchored intermediate oligonucleotide (III) if said protecting group $R_2$ was not previously removed sequentially in any order to form a resulting product; cyclizing the resulting product in the presence of a cyclizing reagent to obtain a cyclized, anchored intermediate of the formula (II);

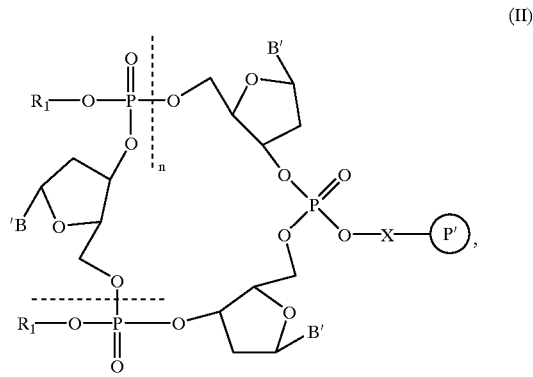

(II)

e) removing the protecting groups $R_1$ from the 3'-phosphate groups in the cyclized anchored intermediate (II), cleaving the cyclized anchored intermediate (II) from the polymeric support and removing the protecting groups of the adenine, cytosine or guanine in said B' groups to form said cyclic oligonucleotide of formula (I); and f) isolating said cyclic oligonucleotide of formula (I), or said salt or said solvate thereof.

2. The process according to claim 1, wherein the protecting group $R_2$ of the 3'-terminal phosphate group is removed before said chain elongation.

3. The process according to claim 1, wherein all of said chain phosphate protecting groups $R_1$ are the same; the 5'-hydroxy protecting groups $R_3$ are the same throughout all of the chain elongation steps; and the adenine, cytosine and guanine in said B' groups are protected in the same way in each of said nucleotides.

4. The process according to claim 1, wherein the 5'-hydroxy protecting groups $R_3$ are selected from the group consisting of 4,4'-dimethoxytrityl (DMT), 4-methoxytrityl (MMT) and 9-(9-phenyl)xantenyl (Pix); the chain phosphate protecting groups $R_1$ are selected from the group consisting of methyl (Me), 2-cyanoethyl (CNE), 2-cyano-1,1-dimethylethyl, allyl and p-nitrophenylethyl; the 3'-terminal phosphate protecting groups $R_2$ are selected from the group consisting of methyl (Me), 2-cyanoethyl (CNE), 2-cyano-1,1-dimethylethyl, allyl and p-nitrophenylethyl; the biradical X of the anchoring group is a benzene ring linked to an oxygen atom of the 3'-terminal phosphate group and to the polymer support (P') by any pair of carbon atoms in the benzene ring and substituted at at least one other carbon atom in the benzene ring by a radical substitutent $R_4$ selected from the group consisting of Cl, Br, $NO_2$ and $-OCH_3$; said spacer/bonding group of said polymeric support (P) is a radical having the formula $-(CH_2)_m-CO-Y-NH-$ wherein m=0 to 6 and Y is, either a simple covalent bond, or a biradical having the formula $-NH-(CH_2)_s-CO-$ wherein s=1 to 10; and the polymeric support (P) is selected from the group consisting of polystyrene-co-1%-divinylbenzene (PS), polyethyleneglycol-polystyrene copolymer (PEG-PS), polyacrylamide, polystyrene-Kel F, polyethyleneglycol, silica gel, controlled pore glass, cellulose and teflon; and the protecting groups of the adenine, cytosine or guanine in said B' are selected from the group consisting of benzoyl (Bz), isobutyryl (iBu), toluoyl, phenylacetyl, phenoxyacetyl, pivaloyl, dimethylaminomethylene, tert-butylphenoxyacetyl and nitrophenylsulfenyl.

5. The process according to claim 4, wherein said $R_2$ is said 2-cyanoethyl and said $R_1$ is said methyl.

6. The process according to claim 4, wherein said $R_2$ is said allyl and said $R_1$ is said 2-cyanoethyl.

7. The process according to claim 4, wherein said $R_1$ and said $R_2$ are both said 2-cyanoethyl provided that said $R_2$ is removed before the chain elongation.

8. The process according to claim 4, wherein said $R_3$ is said 4,4'-dimethoxytrityl (DMT); said benzene ring of said biradical X is linked to the oxygen of the 3'-terminal phosphate at a position 1 of the benzene ring and is linked to the polymeric support (P') at a position 4 of the benzene ring, and said $R_4$ is said Cl and is bonded to the benzene ring at position 2 of the benzene ring; the cyclization reagent is 1-mesitylenesulfonyl-3-nitro-1,2,4-triazole (MSNT); the protecting group of the adenine and the cytosine is said benzoyl (Bz); and the protecting group of the guanine is said isobutyryl (iBu).

9. The process according to claim 4, wherein said m=1 and said s=5 in said spacer/bonding group of said polymeric support.

10. The process according to claim 4, wherein said cyclic oligonucleotide of formula (I) has said n=0 to 20.

11. The process according to claim 1, wherein the polymeric support (P) is selected from the group consisting of polystyrene-co-divinylbenzene (PS) and polyethyleneglycol-polystyrene (PEG-PS).

12. The process according to claim 1, wherein said chain elongation is performed by a phosphite triester method using phosphoramidites.

13. A compound having the formula:

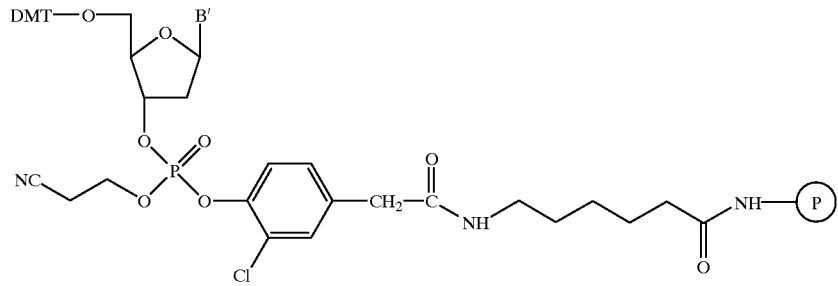

wherein P is a polymeric support and is selected from the group consisting of polystyrene-co-1%-divinylbenzene (PS) and polyethylene glycol-polystyrene (PEG-PS) and B' is a radical selected from the group consisting of adenine, cytosine, guanine, uracil and thymine radicals, and said thymine and said uracil radicals are not protected, but said adenine, cytosine, guanine radicals are protected with a protecting group bound to an exocyclic amine group, and the protecting group of said adenine and said cytosine is benzoyl (Bz) and the protecting group of said guanine is isobutyryl (iBU).

14. A compound having the formula:

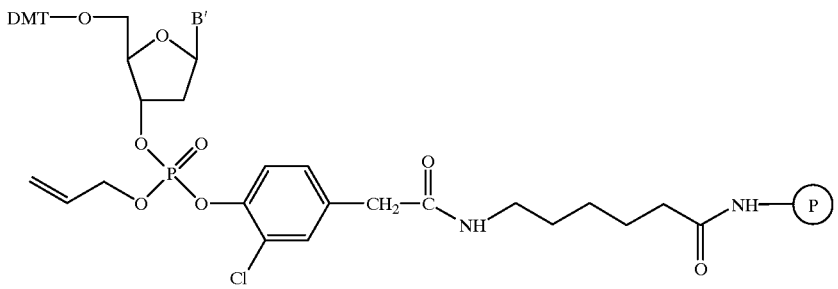

wherein P is a polymeric support and is selected from the group consisting of polystyrene-co-1%-divinylbenzene (PS) and polyethylene glycol-polystyrene (PEG-PS) and B' is a radical selected from the group consisting of adenine, cytosine, guanine, uracil and thymine radicals, and said thymine and said uracil radicals are not protected, but said adenine, cytosine, guanine radicals are protected with a protecting group bound to an exocyclic amine group, and the protecting group of said adenine and said cytosine is benzoyl (Bz) and the protecting group of said guanine is isobutyryl (iBU).

15. A compound having the formula:

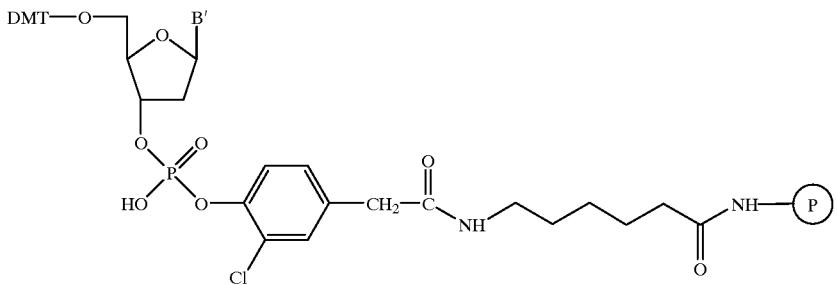

wherein P is a polymeric support and is selected from the group consisting of polystyrene-co-1%-divinylbenzene (PS) and polyethylene glycol-polystyrene (PGE-PS) and B' is a radical selected from the group consisting of adenine, cytosine, guanine, uracil and thymine radicals, and said thymine and said uracil radicals are not protected, but said adenine, cytosine, guanine radicals are protected with a protecting group bound to an exocyclic amine group, and the protecting group of said adenine and said cytosine is benzoyl (Bz) and the protecting group of said guanine is isobutyryl (iBU).

16. A compound consisting of a 2-cyanoethyl 3'-(5'-O-dimethoxytrityl)-2'-deoxynucleosidyl 2-chloro-4-(2,4,5-trichlorophenoxycarbonylmethyl)phenyl phosphate, wherein said 2'-deoxynucleosidyl group includes a nucleobase-containing radical selected from the set consisting of thymine, $N^6$-benzoyl-adenine, $N^4$-benzoylcytosine and $N^2$-isobutyrylguanine (B'=T, $A^{Bz}$, $C^{Bz}$, $G^{iBu}$), said compound having the formula:

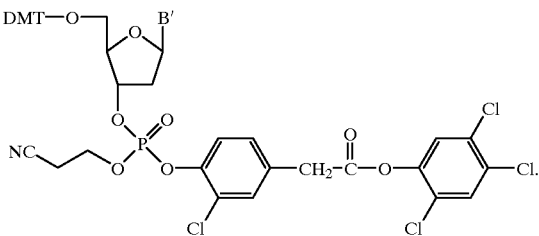

17. A compound which is an allyl 3'-(5'-O-dimethoxytrityl)-2'-deoxynucleosidyl 4-(2,4,5-trichlorophenoxycarbonylmethyl) phenyl phosphate, wherein the 2'-deoxynucleosidyl includes a nucleobase-containing radical selected from the group consisting of thymine, $N^6$-benzoyladenine, $N^4$-benzoylcytosine and $N^2$-isobutyrylguanine(B'=T, $A^{Bz}$, $C^{Bz}$, $G^{iBu}$), said compound having the formula:

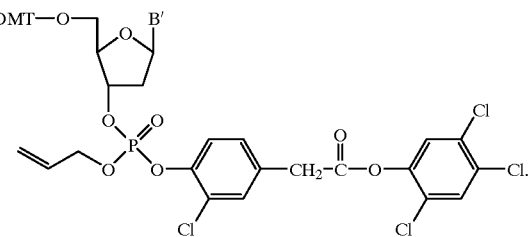

18. A compound consisting of 2,4,5-trichlorophenyl 3-chloro-4-hydroxyphenylacetate of the formula:

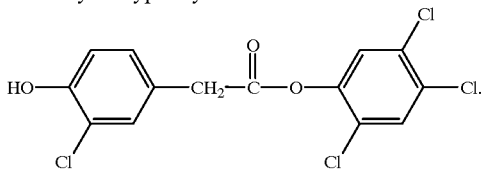

* * * * *